United States Patent [19]

Doorakian et al.

[11] 4,395,574
[45] Jul. 26, 1983

[54] PHOSPHONIUM PHENOXIDE CATALYSTS FOR PROMOTING REACTION OF EPOXIDES WITH PHENOLS AND/OR CARBOXYLIC ACIDS

[75] Inventors: George A. Doorakian, Bedford, Mass.; James L. Bertram, Lake Jackson, Tex.

[73] Assignee: The Dow Chemical Co., Midland, Mich.

[21] Appl. No.: 288,613

[22] Filed: Jul. 30, 1981

Related U.S. Application Data

[60] Division of Ser. No. 148,875, May 12, 1980, Pat. No. 4,302,574, which is a continuation-in-part of Ser. No. 41,567, May 23, 1979, abandoned.

[51] Int. Cl.$^3$ .............................................. C07F 9/54
[52] U.S. Cl. ..................................................... 568/11
[58] Field of Search .......................................... 568/11

[56] References Cited

U.S. PATENT DOCUMENTS 3,442,854  5/1969  Curtius et al. ....................... 528/198
4,340,761  7/1982  Doorakian et al. ................... 568/11

OTHER PUBLICATIONS

Kline et al., "Conductance of Some Onium-type Salts", Chemical Abstracts 41, 4361a (1947).
Wittig et al., "New Synthesis of Cyclopolyenes VI", Chemical Abstracts 53, 16091e (1959).
Schindlbauer, "Molecular and Equivalent Weight Determination of Phosphines and Phosphonium Salts", Chemical Abstracts 59, 10775d (1963).
Schmidbauer et al., "Organosilicon Chemistry of Phosphorus Ylides", Chemical Abstracts 79, 53455q (1973).

*Primary Examiner*—Earl A. Nielsen
*Attorney, Agent, or Firm*—Michael L. Glenn

[57] ABSTRACT

Certain tetrahydrocarbyl phosphonium phenoxide salts are described herein which are novel compounds and/or novel catalysts for promoting the reaction between vicinal epoxides and phenols and/or carboxylic acids or anhydrides. These catalysts are particularly useful in preparing high molecular weight epoxy resins by the advancement reaction of diglycidyl ether of bisphenol A with bisphenol A.

11 Claims, No Drawings

PHOSPHONIUM PHENOXIDE CATALYSTS FOR PROMOTING REACTION OF EPOXIDES WITH PHENOLS AND/OR CARBOXYLIC ACIDS

CROSS-REFERENCE TO RELATED APPLICATION

This is a divisional of application Ser. No. 148,875, filed May 12, 1980, now U.S. Pat. No. 4,302,574, issued Nov. 24, 1981, which is a continuation-in-part of application Ser. No. 041,567, filed May 23, 1979, now abandoned.

BACKGROUND OF THE INVENTION

1. Field of the Invention

This invention relates to novel tetrahydrocarbyl phosphonium phenoxide salts and the preparation of new epoxy-containing materials by a process employing these and other salts as catalysts. In one preferred embodiment, this invention pertains to a process for making a linear, polymeric material having a molecular weight of at least about 100,000 from the advancement reaction of an epoxy resin with a polyhydric phenol (specifically bisphenol A) in the presence of a tetrahydrocarbyl phosphonium bisphenoxide salt.

This invention also relates to precatalyzed epoxy resins and precatalyzed polyhydric phenolic compositions comprising, respectively, an epoxy resin having an average of more than one vicinal epoxide group per molecule or a polyhydric phenol, each composition containing a tetrahydrocarbyl phosphonium phenoxide salt catalyst for promoting the reaction between an epoxide and a phenolic hydroxyl group.

2. Prior Art

It is well-known in the art to produce hydroxyl-containing ethers by reacting a vicinal epoxide with a compound bearing phenolic hydroxyls in the presence of such catalysts as tertiary amines, quaternary ammonium halides, phosphonium halides and the like. See, for example: U.S. Pat. Nos. 2,216,099; 2,633,458; 2,658,855; 3,377,406; 3,477,990; 3,547,881; 3,547,885; 3,694,407; 3,738,862; 3,948,855; and 4,048,141. Canadian Pat. No. 893,191, German Pat. DT Nos. 2,206,218 and 2,335,199 and the text, *Handbook of Epoxy Resins* by H. Lee and K. Neville, McGraw-Hill (1967), *Epoxy Resins-Chemistry and Technology*, Edited by C. Maynard and Y. Tanaka, Marcel-Dekker, Inc. (1973) are also of interest. It is also taught in U.S. Pat. No. 4,048,141 that certain phosphonium catalysts promote the reaction between vicinal epoxides and phenols and/or carboxylic acids or anhydrides.

The prior art catalysts for promoting reactions of epoxides with phenols have generally been deficient in one or more aspects. In many instances, the catalysts react with the epoxy reactant and thus preclude the marketing of a blend comprising an epoxy resin and a catalyst, a so-called "precatalyzed epoxy resin". Blends comprising a polyhydric phenol and a catalyst (i.e., a precatalyzed polyhydric phenol) have likewise been avoided due to possible adverse reactions of the two components. Many prior art catalysts exhibit a lack of selectivity in that they simultaneously promote the reaction of an epoxy resin with both the phenolic hydroxyl group(s) on the reactant and the aliphatic hydroxyl group(s) on the product, which produces branched or cross-linked polymers rather than the desired linear polymers. In still other instances, the reaction rate is unsatisfactory and/or the product is highly colored or contaminated with corrosive anions (e.g., chloride). Moreover, vinyl ester resins made from the catalyzed reaction products of epoxy resins and polyhydric phenols in the presence of most prior art catalysts require undesirably long cure times because of the presence of relatively high concentrations of phenolic hydroxyl groups.

The prior art catalysts, to a greater or lesser degree, produce at best linear or substantially linear polymers of relatively limited molecular weights. For example, the advancement reaction of 4,4'-isopropylidenediphenol (i.e., bisphenol A) with a diglycidyl ether of bisphenol A in the presence of a triphenyl ethyl phosphonium acetate salt-acetic acid complex even when followed by further reaction with tetrabromobisphenol A produces a linear polymer with a maximum weight average molecular weight of about 60,000 as determined by gel permeation chromatography. These deficiencies have now been remedied by the subject invention.

SUMMARY OF THE INVENTION

It has now been discovered that tetrahydrocarbyl phosphonium phenoxide salts represented by the formula

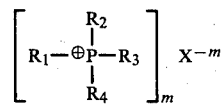  I wherein $R_1$–$R_4$ each independently is a hydrocarbyl or inertly-substituted hydrocarbyl, "X" is a phenoxide anion, and "m" is the valence of the anion "X", are novel catalysts for promoting the reaction between vicinal epoxides and carboxylic acids or anhydrides or aromatic compounds bearing nuclear hydroxyl groups.

The term phenoxide as used herein denotes a conjugate base of an aromatic carbocyclic compound bearing at least one nuclear hydroxyl group. The tetrahydrocarbyl phosphonium phenoxide salts include those salts complexed with one or more moles of an aromatic carbocyclic hydroxyl compound $H_mX$, wherein X and m are defined as above. These salts also include salts complexed with one or more moles of a tetrahydrocarbyl phosphonium hydroxide salt.

These novel catalysts are surprisingly effective in selectively catalyzing the desired reaction at a suitable reaction rate. Reaction products can be obtained in high conversion and are of excellent color. When the novel compound represented by Formula I, in which X is derived from a polyhydric phenol is used as an advancement catalyst, linear reaction products can be prepared with weight average molecular weights substantially exceeding those effected by prior art methods.

Additionally, the novel catalysts are surprisingly unreactive with epoxy resins or polyhydric phenols at conventional storage temperatures. As a result, a precatalyzed epoxy resin or polyhydric phenol can be prepared, respectively, by blending the subject catalyst with an epoxy resin or polyhydric phenol. Such precatalyzed epoxy resins or polyhydric phenols are, of course, novel compositions of matter.

DETAILED DESCRIPTION OF THE INVENTION

Phosphonium Phenoxide Salts

Representative tetrahydrocarbyl phosphonium phenoxide salts are represented by formula II or IV. Phenol complexes of these salts are represented by formula III and V–VII. In formulae II–VII, $R_1$–$R_4$ and X are defined as in Formula I.

$$R_1R_2R_3R_4P^{\oplus}X^{\ominus} \qquad \text{II}$$

$$R_1R_2R_3R_4P^{\oplus}X^{\ominus}.HX \qquad \text{III}$$

$$(R_1R_2R_3R_4P^{\oplus})_2X^{\ominus} \qquad \text{IV}$$

$$(R_1R_2R_3R_4P^{\oplus})_2X^{\ominus}H_2X \qquad \text{V}$$

$$(R_1R_2R_3R_4P^{\oplus})_2X^{\ominus}2H_2X \qquad \text{VI}$$

$$(R_1R_2R_3R_4P^{\oplus})_2X^{\ominus}3H_2X \qquad \text{VII}$$

Where the phenoxide anion is derived from a monohydric phenol, the tetrahydrocarbyl phosphonium phenoxide salt may take the form represented by formulae II or III. If X is derived from a dihydric phenol, the possible compounds are represented by formulae II–VII. Of course, other salts and complexes are possible where the phenoxide anion is derived from a trihydric aromatic hydroxyl compound or a higher polyhydric aromatic hydroxyl compound. We believe that formula II represents the typical phosphonium phenoxide salts.

The tetrahydrocarbyl phosphonium phenoxide salts complexed with tetrahydrocarbyl phosphonium hydroxide salts have the following formula, wherein $R_1$–$R_4$ and X are as previously defined, $$R_1R_2R_3R_4P^{\oplus}X^{\ominus}.P^{\oplus}R_1R_2R_3R_4OH^{\ominus}.$$

Generally, such complexes have been observed where X is a monoanion derived from a dihydric or polyhydric phenol.

The phenoxide anion, X, is a conjugate base of a phenol or other aromatic carbocyclic hydroxyl compound, said phenol being an organic compound having an aromatic mono- or polycyclic hydrocarbon nucleus bearing one or more hydroxyl groups. The phenoxide anion, phenoxide dianion and higher phenoxide anions are distinguished from the corresponding phenol or other aromatic hydroxyl compounds in that one or more of the phenolic or other aromatic hydroxyl groups are deprotonated in the former. The phenoxide anion can be generally represented by the formula

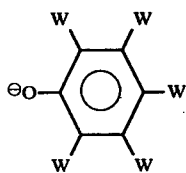

wherein each W independently is an oxide anion, hydrogen, carboxyl, halo, hydrocarbyl, nitro or hydroxyl moiety. Where W is a hydrocarbon substituent it can bear or contain one or more benzene rings bearing phenolic hydroxyl, phenoxide anion, halo, nitro, hydrogen or carboxyl moieties.

Representative phenoxide anions include conjugate bases of phenol, α- and β-naphthol, o-, m-, or p-chlorophenol, 2-hydroxybiphenyl, alkylated derivatives (e.g., o-methyl-, 3,5-dimethyl-, p-t-butyl- and p-nonylphenol), other monohydric phenols, or a halogenated or nitrated derivative thereof, as well as polyhydric phenols, such as resorcinol, hydroquinone, phenolphthalein, etc. In one embodiment, the phenoxide anion, X, can be the conjugate base of an epoxy resin bearing at least one terminal phenolic hydroxyl group. Where the phosphonium phenoxide salt is utilized as a catalyst for the advancement of a polyepoxide, the anion, X, is desirably a conjugate base of the phenol to be reacted with the polyepoxide reactant.

Tetrahydrocarbyl phosphonium salts of polyhydric phenols are novel compounds, which are preferred as catalysts. Preferred phenoxide anions and phenoxide dianions are those which are conjugate bases and diconjugate bases, respectively, of polyhydric phenols bearing from 2 to 6 nuclear hydroxyl groups and having from about 12 to about 30 carbon atoms, because the novel phosphonium salts containing these anions are particularly effective as catalysts in preparing ultra-high molecular weight epoxy resins. Representative examples of such preferred anions include the phenoxides and bisphenoxides of phenolphthalein, 2,4',4''-tri(hydroxyphenyl)methane (i.e., trisphenol) and the compound corresponding to the formula

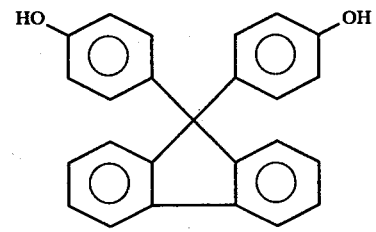

Particularly preferred are the conjugate bases and diconjugate bases of polyhydric phenols corresponding to the formula

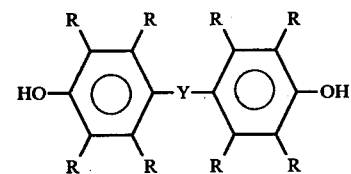

VIII wherein each R independently is a hydrogen, halogen, hydrocarbyl, inertly-substituted hydrocarbyl or hydrocarbyloxy group, and Y is a single covalent bond, oxygen, sulfur, —CO—, —SO—, —SO$_2$—, lower alkylene or alkylidene of from 1 to 6 carbon atoms, inclusive. In one embodiment, Y is a hydrocarbon radical consisting essentially of oxyarylene-oxy(1,3-(2-hydroxy)alkylene units, so that the comound of formula VIII is an epoxy resin prepolymer terminated with two phenolic hydroxyl groups, said prepolymer having a substantially linear backbone. More preferably, each R independently is hydrogen, chlorine or bromine and Y is a C$_1$–C$_4$ alkylene or alkylidene; most preferably, Y is methylene or isopropylidene. The most preferred phenoxide anions and dianions are those derived from bisphenol A (4,4'-isopropylidenediphenol), bisphenol F (4,4'-methylenediphenol), 2,2',6,6'-tetrachlorobisphenol A, 2,2',6,6'-tetrabromobisphenol A, bisphenol S (4,4'- sulfonyldiphenol) and 2,2',6,6'-tetrabromo-4,4'-sulfonyldiphenol.

In both the salts and the complexes, $R_1$-$R_4$ independently are preferably phenyl, benzyl, alkyl or inertly-substituted alkyl of from 1 to 12 carbon atoms and more preferably are phenyl or a $C_1$-$C_4$ alkyl. Illustrative examples of the instant class of novel compounds include: tetraphenyl-, triphenyl methyl-, triphenyl ethyl-, triphenyl n-butyl-, triphenyl benzyl-, tetra-n-butyl-, tri-n-butyl methyl-, tri-n-butyl benzyl, tri-(cyanoethyl)methyl-, tri-(hydroxymethyl)methyl-phosphonium phenoxide salts, the analogous di(tetrahydrocarbyl phosphonium)bisphenoxide salts or phenolic complexes of said salts and the like. More preferably $R_1$-$R_4$ are each independently phenyl or n-butyl groups. Most preferably these tetrahydrocarbyl groups are triphenyl n-butyl or triphenyl ethyl groups.

Compounds of formula I are conveniently prepared by reacting, at a temperature of about 0° C. to 25° C., a tetrahydrocarbyl phosphonium halide dissolved in a lower alkanol, water or mixtures thereof with an ion-exchange resin of the quaternary ammonium, hydroxide-type, to thereby produce a solution containing the corresponding tetrahydrocarbyl phosphonium hydroxide salt. The reaction is most efficiently carried out by passing the phosphonium halide solution through a column packed with the ion-exchange resin; however, a batchwise procedure can also be used. In an alternate procedure, the tetrahydrocarbyl phosphonium halide is reacted with an alkali metal hydroxide in a liquid medium to produce the tetrahydrocarbyl phosphonium hydroxide. A phenol is then added to the tetrahydrocarbyl phosphonium hydroxide solution, in generally a stoichiometric ratio so as to produce a tetrahydrocarbyl phosphonium phenoxide salt, or a phenol complex of said salt. Completion of this reaction can be determined by monitoring the pH of the solution. The phosphonium salt can be separated by filtration, if a precipitate, or the solvent can be removed by distillation to recover the solid salt.

In still another process, the tetrahydrocarbyl phosphonium halide can be mixed with a phenol in a liquid medium followed by addition of an alkali metal hydroxide to produce the tetrahydrocarbyl phosphonium phenoxide salt or a phenol complex of said salt. This latter method is the method of choice for preparing the preferred tetrahydrocarbyl phosphonium catalysts having phenoxide or bisphenoxide anions, such as those derived from bisphenol A.

If 0.5 mole of a phenol is reacted with each mole of the tetrahydrocarbyl phosphonium hydroxide, a tetrahydrocarbyl phosphonium phenoxide salt complexed with tetrahydrocarbyl phosphonium hydroxide will be produced. Of course, if a smaller excess of the phosphonium hydroxide is employed, all of the salt will not be complexed. In particular, such complexes have been observed where the phenol reactant is dihydric or polyhydric, such as bisphenol A or bisphenol S. Generally the uncomplexed salt can be recovered by treating the solid, phosphonium hydroxide complex with acetone. These phosphonium hydroxide complexes are in some instances somewhat less stable than the corresponding tetrahydrocarbyl phosphonium phenoxide salt. For example, a triphenylethyl phosphonium salt of bisphenol A complexed with the corresponding phosphonium hydroxide had a half-life of three days at 60° C. in a 50 weight percent methanol solution. On the other hand, the corresponding phosphonium salt of bisphenol S complexed with triphenylethyl phosphonium hydroxide did not decompose to ethyl diphenyl phosphine oxide to any significant degree during a 25-day period at 60° C. in a methanol solution. The aforementioned tetrahydrocarbyl phosphonium hydroxide complexes are advantageous as advancement catalysts, because they are generally more soluble in organic solvents, such as methanol, than are the tetrahydrocarbyl phosphonium phenoxide salts. Hence, these complexes are more readily dispersed in an advancement reaction medium containing an organic solvent.

If the phenol reactant has a pKa (of the first hydroxyl group deprotonated) greater than about 7.5, for example bisphenol A (pKa 10.0), then a phenol complex (formulae III or VII) of the phosphonium salt is preferentially isolated from the reaction of the phenol with no more than an equimolar amount of the phosphonium hydroxide. This solid phenol complex is termed a 1:2 salt because one mole of the phosphonium cation is present with two moles of the phenol (whether as a phenoxide anion or phenol adduct). On the other hand, if the phenol reactant has a pKa less than about 7.5, for example, 2,2',6,6'-tetrabromo-4,4'-isopropylidenediphenol (pKa 6.8), the tetrahydrocarbyl phosphonium phenoxide salt or di(tetrahydrocarbyl phosphonium)-bisphenoxide salt or its phenol complex will be the predominant product isolated. These products are 1:1 phosphonium salts. A large number of acid dissociation constant values are listed in the chapter by H. C. Brown et al. in "Determination of Organic Structures by Physical Methods", Academic Press (1955), edited by E. A. Braude and F. C. Nachod, which is herein incorporated by reference. The analytical data available does not resolve whether the tetrahydrocarbyl phosphonium phenoxide salt or the di(tetrahydrocarbyl phosphonium)bisphenoxide salt or a phenol complex predominates or is the sole species present at equilibrium in a solution.

The phosphonium phenoxide salts and their phenol and phosphonium hydroxide complexes are generally white or light-yellow, crystalline solids having distinct melting points and low vapor pressure. These solids are generally soluble or slightly soluble in moderately polar solvents, such as acetone, methanol, ethanol, phenol, isopropanol, liquid epoxy resins and the like. These compounds are also generally insoluble in benzene, toluene and water.

Epoxide Reactants

The vicinal epoxide reactants are organic compounds bearing one or more moieties corresponding to the formula

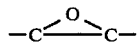

The alkylene oxides of from 2 to about 24 carbon atoms, the epihalohydrins and the epoxy resins are perhaps the best known and most widely used members of the genus. Ethylene oxide, 1,2-propylene oxide, 1,2-butylene oxide and epichlorohydrin are the preferred monoepoxides. These alkylene oxides can be reacted with monohydric phenols to prepare useful alkylene glycol phenyl ethers, e.g., $(C_6H_5)$—$OCH_2CH_2$—OH, in the presence of the above-described catalysts. Similarly, monoepoxides can be reacted with carboxylic acids and anhydrides to prepare other useful products.

The most useful epoxy reactants are the polyepoxides, particularly epoxy resins. These polyepoxides are reacted with polyhydric phenols (compounds having more than one phenolic hydroxy group) to form a phenolic hydroxy ether in the so-called advancement reaction. The polyepoxide reactants are organic compounds possessing more than one 1,2-epoxide group per molecule. These polyepoxides can be saturated or unsaturated aliphatic or cycloaliphatic, aromatic or heterocyclic in nature. Additionally, the polyepoxides can bear substituents which are inert in the advancement reaction, such as ether or halogen moieties.

The polyepoxides are conveniently described in terms of epoxy equivalent values, as defined in U.S. Pat. No. 2,633,458. The polyepoxides used in the subject advancement reaction are those having an epoxy equivalency greater than 1.0.

Various examples of polyepoxides that may be used in the invention are given in U.S. Pat. No. 2,633,458 and it is to be understood that so much of the disclosure of that patent relative to examples of polyepoxides is incorporated by reference into this specification.

Other examples of polyepoxides include the glycidyl ethers of novolac resins, i.e., phenol-aldehyde condensates. Preferred resins of this type are those of the formula:

Other examples of polyepoxides include the epoxidized esters of the polyethylenically unsaturated monocarboxylic acids, such as epoxidized linseed, soybean, perilla, oiticica, tung, walnut and dehydrated castor oil, methyl linoleate, butyl linoleate, ethyl 9,12-octadecanedioate, butyl 9,12,15-octadecanetrioate, butyl oleostearate, mono- or diglycerides of tung oil, monoglycerides of soybean oil, sunflower oil, rapeseed oil, hempseed oil, sardine oil, cottonseed oil, and the like.

Another group of the epoxy-containing materials used in the process of the invention include the epoxidized esters of unsaturated monohydric alcohols and polycarboxylic acids, such as, for example, diglycidyl phthalate, diglycidyl adipate, diglycidyl isophthalate, di(2,3-epoxybutyl)adipate, di(2,3-epoxybutyl)oxalate, di(2,3-epoxyhexyl)succinate, di(3,4-epoxybutyl)maleate, di(2,3-epoxyoctyl)pimelate, di(2,3-epoxybutyl)phthalate, di(2,3-epoxyoctyl)tetrahydrophthalate, di(4,5-epoxydodecyl)maleate, di(2,3-epoxybutyl)terephthalate, di(2,3-epoxypentyl)thiodipropionate, di(5,6-epoxytetradecyl)diphenyldicarboxylate, di(3,4-epoxyheptyl)sulfonyldibutyrate, tri(2,3-epoxybutyl)1,2,4-butanetricarboxylate, di(5,6-epoxypentadecyl)tartrate, di(4,5-epoxytetradecyl)maleate, di(2,3-epoxybutyl)azelate, di(3,4-epoxybutyl)citrate, di(5,6-epoxyoctyl)cyclohexane-1,3-dicarboxylate, di(4,5-epoxyoctadecyl)malonate.

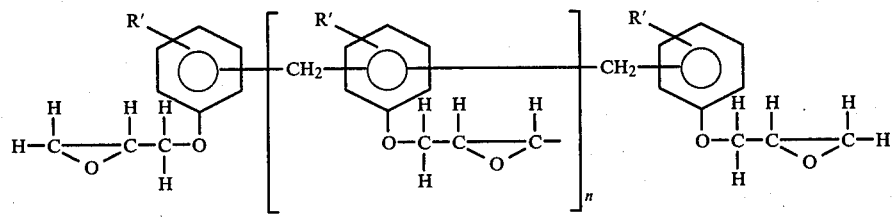

IX wherein each R' independently is hydrogen or an alkyl radical and n has an average value of from about 0.1 to about 10, preferably from about 1 to about 2. Preparation of these polyepoxides is illustrated in U.S. Pat. Nos. 2,616,099 and 2,658,885.

The preferred polyepoxides are those represented by the general formula

Another group of the epoxy-containing materials include those epoxidized esters of unsaturated alcohols and unsaturated carboxylic acids, such as glycidyl glycidate, 2,3-epoxybutyl 3,4-epoxypentanoate; 3,4-epoxyhexyl 3,4-epoxypentanoate; 3,4-epoxy-6-methylcyclohexylmethyl 3,4-epoxy-6-methylcyclohexane carboxylate.

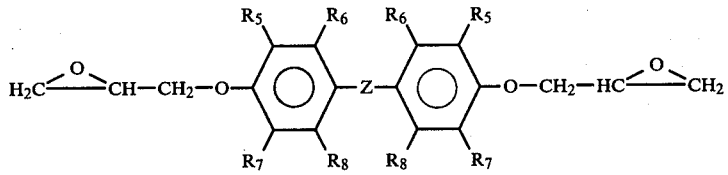

XI wherein $R_5$, $R_6$, $R_7$ and $R_8$ are each independently selected from hydrogen, bromine and chlorine and wherein Z is selected from oxygen, sulfur, —SO—, —SO$_2$—, bivalent hydrocarbon radicals containing up to about 10 carbon atoms, oxygen-, sulfur- and nitrogen-containing hydrocarbon radicals, such as —OR'O—, —OR'—O—R'—O—, —S—R'—S—, and

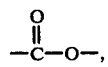

wherein R' is a bivalent hydrocarbon radical at each occurrence. "Z" preferably is an alkylene or alkylidine group having from about 1 to about 4 carbon atoms.

Still another group of the epoxy-containing materials includes epoxidized derivatives of polyethylenically unsaturated polycarboxylic acids, such as, for example, dimethyl 8,9,12,13-diepoxyeicosanedioate; dibutyl 7,8,11,12-diepoxyoctadecanedioate; dioctyl 10,11-diethyl-8,9,12,13-diepoxyeicosanedioate; dihexyl 6,7,10,11-diepoxyhexadecanedioate; didecyl 9-epoxyethyl-10,11-epoxyoctadecanedioate; dibutyl 3-butyl-3,4,5,6-diepoxycyclohexane-1,2-dicarboxylate; dicyclohexyl 3,4,5,6-diepoxycyclohexane-1,2-dicarboxylate; dibenzyl 1,2,4,5-diepoxycyclohexane-1,2-dicarboxylate and diethyl 5,6,10,11-diepoxyoctadecyl succinate.

Still another group comprises the epoxidized polyethylenically unsaturated hydrocarbons, such as epoxidized 2,2-bis(2-cyclohexenyl)propane, epoxidized vinyl cyclohexene and epoxidized dimer of cyclopentadiene.

Phenolic Reactants

The phenolic reactants are organic compounds having one or more hydroxyl groups attached to an aromatic carbocyclic nucleus. This class of compounds therefore includes phenol, alpha and beta naphthol, o-, m-, or p-chlorophenol, alkylated derivatives of phenol (e.g. o-methyl-, 3,5-dimethyl-, p-t-butyl- and p-nonyl-phenol) and other monohydric phenols as well as polyhydric phenols, such as resorcinol, hydroquinone, etc.

The polyhydric phenols bearing from 2 to 6 hydroxyl groups and having from 6 to about 30 carbon atoms are particularly useful as reactants in the reaction with epoxy resins to form high molecular weight resins. Representative of these preferred phenols are 2,4',4"'-tri(hydroxyphenyl)methane, phenolphthalein and the like. Particularly preferred as phenol reactants are those compounds corresponding to formula VIII. The most preferred phenols are bisphenol A, bisphenol F, 2,2',6,6'-tetrachlorobisphenol A, 2,2',6,6'-tetrabromobisphenol A, and bisphenol S.

The Carboxylic Acid Reactants

The organic carboxylic acids and anhydrides are likewise well known. The acids bear one or more carboxyl groups on the organic nucleus. The anhydrides are prepared from such carboxylic acids by the removal of water therefrom in an intra- or intermolecular condensation. This class of compounds therefore includes acetic, propionic, octanoic, stearic, acrylic, methacrylic, oleic, benzoic, phthalic, isophthalic, maleic, succinic, adipic, itaconic, polyacrylic and polymethacrylic acids, and the like, and anhydrides thereof, such as acetic anhydride, phthalic anhydride, hexahydrophthalic anhydride, etc.

A preferred subclass of acids is comprised of members which are useful in cross linking epoxy resins. The members of this subclass are normally di- or tribasic acids, or anhydrides thereof, and are preferably liquid or low melting solids such as succinic, maleic, or hexahydrophthalic acids or anhydrides and the like. Other such acids and anhydrides are shown, for example, in U.S. Pat. No. 2,970,983 and U.S. Pat. No. 3,547,885.

Process for Reacting Epoxide and Phenol

The reaction conditions employed in the process may be varied. Generally, however, convenient rates of reaction are obtained at reaction temperatures in the range of from about 50° C. to about 300° C. and reaction pressures ranging from about atmospheric to about 150 psig.

The ratio of the epoxide to the phenol or carboxylic acid or anhydride reactants to be employed in the process may vary over a wide range depending upon the type of reactants and the type of product desired. For example, if a product terminated with a phenolic ether group is desired, one would employ an excess of the phenol in the process.

The amount of the phosphonium catalyst employed in the process of this invention can likewise vary over a wide range, so long as a catalytic amount is present. In general, the catalyst is added in amounts of from about 0.001 percent to about 10 percent, preferably from about 0.05 percent to about 5 percent, by weight of the reactants.

The reaction may be conducted in the presence or absence of solvents or diluents, but is conveniently conducted in a liquid phase. In most cases, the reactants will be liquid or low melting solids and the reaction may be at least initially easily effected without the addition of solvents or diluents. As the advancement reaction proceeds and the average molecular weight of the product increases, the reaction mixture becomes progressively more viscous or may solidify. To maintain efficient blending of the reaction mixture, it may be necessary to add diluents, increase the temperature of the reaction mixture to the fusion point of the reactants or to utilize very efficient blending means. Suitable diluents are those organic compounds which are inert to the reactants and in the liquid phase at the reaction temperature, for example, ethylene glycol ethyl ether, methyl ethyl ketone, acetone, xylene, toluene, cyclohexane and the like. The diluent is desirably substantially free of impurities which will decrease the activity of the catalyst, such as hydrogen peroxide or uncomplexed transition metal ions.

If solvents are employed in the reaction and the resulting product is to be used for coating purposes, the solvent may be retained in the reaction mixture. Otherwise, the solvent can be removed by any suitable method such as distillation and the like.

One particularly advantageous embodiment of the instant process is the use of tetrahydrocarbyl phosphonium salts of polyhydric phenols as a catalyst in the advancement reaction to produce ultra-high molecular weight resins and polymers. Advantageously, the phenoxide anion of the catalyst is the conjugate base or diconjugate base of a phenol corresponding to Formula VII. To produce the ultra-high molecular weight resins relatively greater catalyst loadings must be employed than to produce resins of molecular weights less than about 100,000 molecular weight with these same catalysts. The advancement reaction can be advantageously conducted in a high boiling, inert, organic diluent, such as a derivative of ethylene glycol, for example ethylene glycol ethyl ether and the like. Desirably, substantially equivalent quantities of polyhydric phenol and polyepoxide reactants should be employed in the overall reaction (i.e., no more than about 2 percent excess of either reactant). As the reaction between the polyepoxide and the polyhydric phenol approaches completion, it is desirable, but not essential, to introduce sufficient tetrabromobisphenol A to react the vicinal epoxy groups completely and to increase molecular weight of the product in the manner taught in U.S. Pat. No. 4,104,257.

Advancement Reaction Products

The products obtained according to the above process of reacting a polyepoxide with a phenol in the presence of the desired phosphonium catalysts in a process are phenolic hydroxy ether compounds. Their physical characteristics will depend upon the reactants and proportions employed. In general, the products will vary from liquids to solids, and in the case of the high molecular weight resins will vary from viscous liquids to hard solids. The products will possess an aliphatic OH group formed by each reaction of an epoxide and a phenolic OH group, and can be further reacted through this group if desired. The polyfunctional reactants will also give products terminated in phenolic OH groups and/or epoxy groups, and these will be available for further reaction.

The control of the equivalent ratio of the polyepoxides and polyhydric phenols during the advancement reaction permits the preparation of a variety of products. Those products which use an excess of the polyepoxide in their preparation will be terminated in epoxy groups and can be used as polyepoxides in known reactions of polyepoxides with curing agents and the like. The high molecular weight polyepoxides are particularly useful in preparing surface coatings, adhesives, laminates, filament windings, coatings for highways and airfields, structural applications, formation of foams and the like. Those prepared from the halogenated polyhydric phenols as shown hereinafter are particularly useful as flame proofing resins for forming laminates, coatings and the like. The ultra-high molecular weight product terminated with a phenolic ether group approaches an engineering thermoplastic, like polycarbonate, in some of its properties and is particularly suited to such uses as an automotive undercoating, films or molded articles. This novel polymer is linear or substantially linear, consists essentially of oxyarylene-oxy(1,3-(2-hydroxy)alkylene) units (wherein the arylene moiety is the aromatic portion of the polyhydric phenol reactant) and said polymer has a weight average molecular weight of at least about 100,000. The polymeric product can be used as produced by the in-situ process or the polymer can be precipitated from methanol to remove catalyst by-products and monomeric impurities.

The reaction products terminated in epoxy groups can also be used to prepare vinyl ester resins. Vinyl ester resins are described in U.S. Pat. No. 3,367,992 wherein dicarboxylic acid half esters of hydroxyalkyl acrylates or methacrylates are reacted with polyepoxide resins. Bowen in U.S. Pat. Nos. 3,066,112 and 3,179,623 describes the preparation of vinyl ester resins from unsaturated monocarboxylic acids such as acrylic and methacrylic acid. Vinyl ester resins based on epoxy novolac resins are described in U.S. Pat. No. 3,301,743 to Fekete et al. Fekete et al. also describe in U.S. Pat. No. 3,256,226 vinyl ester resins wherein the molecular weight of the polyepoxide is increased by reacting a dicarboxylic acid with the polyepoxide resin as well as acrylic acid, etc. Other difunctional compounds containing a group which is reactive with an epoxide group, such as an amine, mercaptan, and the like, may be utilized in place of the dicarboxylic acid. All of the above-described resins, which contain the characteristic linkages

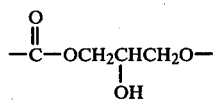

and terminal, polymerizable vinylidene groups, are classified as vinyl ester resins, and are incorporated herein by reference.

The unsaturated monocarboxylic acids which can be reacted with a polyepoxide in the presence of the described catalysts to prepare a vinyl ester resin include acrylic acid, methacrylic acid, halogenated acrylic acid or methacrylic acid, cinnamic acid and the like and mixtures thereof, and hydroxyalkyl acrylate or methacrylate half esters of dicarboxyl acids as described in U.S. Pat. No. 3,367,992 wherein the hydroxyalkyl group preferably has from 2 to 6 carbon atoms.

Precatalyzed Epoxy Resins and Precatalyzed Polyhydric Phenols

Precatalyzed epoxy resin and precatalyzed polyhydric phenol compositions are of particular commercial interest. Precatalyzed epoxy resin compositions are blends of an epoxy resin and an effective amount of an advancement catalyst, which when combined with a polyhydric phenol at reactive conditions produce epoxy resins of increased molecular weight. Similarly, precatalyzed polyhydric phenols are blends of a polyhydric phenol and an effective amount of an advancement catalyst. In the case of a normally solid polyhydric phenol, such as bisphenol A, it is advisable to first melt the phenol and then to add the catalyst to the liquid phenol to obtain a homogeneous mixture. The catalysts previously described are particularly suited for this use.

The following examples are illustrative of the present invention and are not to be construed as limiting the scope thereof in any manner. All parts and percentages are by weight unless otherwise specified.

EXAMPLE 1

A solution of 100 grams of n-butyl triphenylphosphonium bromide in 40 grams of methanol is percolated through a tightly packed column of 509 grams of a quaternary ammonium-type, styrene-divinylbenzene anion exchange resin (sold under the tradename Dowex SBR) bearing 3.5 milliequivalents per gram of exchangeable hydroxide groups. The methanol solution is found by conventional methods of analysis to contain 20.7 percent of n-butyl triphenyl phosphonium hydroxide salt and less than 0.05 percent bromine.

A solution of 78.8 grams (0.145 mole) of 2,2',6,6'-tetrabromobisphenol A in 50 grams of methanol is added with stirring at 20° C. to 48.8 grams (0.145 mole) of the n-butyl triphenyl phosphonium hydroxide salt in 236.0 grams of methanol solvent. After stirring the reaction mixture for thirty minutes, the mixture is filtered to collect a white precipitate. The collected precipitate is dried to yield 122.5 grams of a crude product having a melting point of 218° C.-220° C. The product is then washed with acetone. Conventional methods of analysis (infrared spectroscopy, elemental analysis and proton, carbon-13 and phosphorus nuclear magnetic resonance) are utilized to identify the product as a 1:1 n-butyl triphenyl phosphonium salt of 2,2',6,6'-tetrabromobisphenol A. The yield of the identified product based on the corresponding phosphonium hydroxide salt is 98.0 mole percent.

EXAMPLE 2

In a manner otherwise similar to that described in Example 1, a methanol solution of 66.2 grams (0.29 mole) of bisphenol A is added to a stirred methanol solution containing 48.8 grams (0.145 mole) of the n-butyl triphenyl phosphonium hydroxide salt. A white crystalline precipitate is collected and dried to a constant weight of 103.97 grams. The melting point of the crude product is 153° C.-155° C. Conventional methods of analysis are utilized to identify the product as a 1:2 n-butyl triphenyl phosphonium salt complex of bisphenol A. The yield of the identified product based on the corresponding phosphonium hydroxide salt is 92.4 mole percent.

When equimolar amounts of the n-butyl triphenyl phosphonium hydroxide salt and bisphenol A are employed in the methanol reaction medium a 1:2 n-butyl triphenyl phosphonium salt of bisphenol A is still isolated.

EXAMPLE 3

In a manner otherwise similar to that described in Example 1, a methanol solution of 53.09 grams (0.145 mole) of tetrachlorobisphenol A is added to 48.8 grams (0.145 mole) of the n-butyl triphenyl phosphonium hydroxide salt. A white crystalline precipitate, having a dry weight of 97.75 grams, is collected. Conventional methods of analysis are utilized to identify the product as a 1:1 n-butyl triphenyl phosphonium salt of 2,2',6,6'-tetrachlorobisphenol A. The yield of the identified product is 98.5 mole percent.

EXAMPLE 4

In a manner otherwise similar to that described in Example 1, a methanol solution of 4.09 grams (0.024 mole) of 2-hydroxybiphenyl is added to a stirred methanol solution of 4.06 grams (0.012 mole) of the n-butyl triphenyl phosphonium hydroxide salt. The methanol solvent is distilled from the reaction mixture and the remaining 6.64 grams of a light-yellow solid washed with acetone. The solid is identified by conventional methods of analysis as a 1:2 n-butyl triphenyl phosphonium salt complex of 2-hydroxybiphenyl. The yield of the identified product is 84.0 mole percent.

EXAMPLE 5

In a manner otherwise similar to that described in Example 1, a methanol solution of 3.03 grams (0.024 mole) of 1,3,5-trihydroxybenzene is added to a stirred methanol solution of 4.06 grams (0.012 mole) of the n-butyl triphenyl phosphonium hydroxide salt. The methanol solvent is distilled from the reaction mixture and the remaining 6.7 grams of tan solid washed with acetone. Conventional methods of analysis are utilized to identify the product as a 1:2 n-butyl triphenyl phosphonium salt complex of 1,3,5-trihydroxybenzene. The yield of the identified product is 98.0 mole percent.

EXAMPLE 6

A solution of 140 grams of tetra(n-butyl)phosphonium bromide in 56 grams of methanol is percolated through a tightly packed column of 509 grams of a quaternary ammonium-type, styrene-divinylbenzene anion exchange resin (sold under the tradename Dowex SBR) bearing 3.5 milliequivalents per gram of exchangeable hydroxide groups. The column is flushed with additional quantities of methanol, which are combined with the first methanol solution. The resulting methanol solution is determined to contain 17.0 percent of tetrabutyl phosphonium hydroxide salt.

In a manner otherwise similar to Example 1, a methanol solution of 44.47 grams (0.195 mole) of bisphenol A is added to a stirred methanol solution containing 27 grams (0.0975 mole) of tetrabutyl phosphonium hydroxide salt. A white crystalline precipitate is collected and dried to a constant weight of 68.1 grams. The melting point of the crude product is 218° C.–221° C. Conventional methods of analysis are utilized to identify the product as a 1:2 tetra(n-butyl)phosphonium salt of bisphenol A. The yield of the identified product is 95.3 mole percent.

EXAMPLES 7-11

In a manner otherwise similar to that described in Example 6, the phenols listed in Table I are reacted with tetra(n-butyl)phosphonium hydroxide salt. The crude product is then isolated from the methanol reaction mixture, dried and weighed. Conventional methods of analysis are utilized to identify the product and in each instance the product is a tetra(n-butyl)phosphonium salt of the phenol reacted as expected. The mole ratio of the tetra(n-butyl)phosphonium hydroxide salt ($R_4P^{\oplus}{}^{\ominus}OH$) to the phenol (HX) added to the reaction mixture, the mole ratio of the tetra(n-butyl)phosphonium cation to the total phenoxide and phenol in the product salt, the isolated yield of the product in mole percent and the pKa of the phenol reactant are also tabulated in Table I.

TABLE I

| Example | Phenol | Reaction Mole Ratio $R_4P^{\oplus}{}^{\ominus}OH{:}HX$ | Salt Mole Ratio $R_4P^{\oplus}{:}(HX + X^{\ominus})$ | Isolated Yield | pKa |
|---|---|---|---|---|---|
| 7 | 2,2',6,6'-Tetrabromo bisphenol A | 1:1 | 1:1 | 81.5 | 6.8 |
| 8 | Pentachlorophenol | 1:1 | 1:1 | 97.0 | 4.6 |
| 9 | 4,6-Dinitro-2-sec-butyl-phenol | 1:1 | 1:1 | 94.0 | 4.4 |
| 10 | 4,4'-Thiodiphenol | 1:2 | 1:2 | 98.0 | 10.3 |
| 11 | 4-t-Butyl-phenol | 1:2 | 1:2 | 62.4 | * |
| 12 | 4,4'-sulfonyldiphenol | 1:2 | 1:2 | 97.5 | 7.8 |

*Not determined

EXAMPLES 13-22

In a manner otherwise similar to that described in Example 1, several tetrahydrocarbyl phosphonium chloride ($R_4P^{\oplus}Cl^{\ominus}$) salts listed in Table II are percolated through an ion-exchange column to produce the corresponding hydroxide salts. These tetrahydrocarbyl phosphonium hydroxide salts are then reacted with the phenol reactants (HX) tabulated in Table II in the appropriate mole ratios to produce the corresponding tetrahydrocarbyl phosphonium salt of the phenol reacted, as is confirmed by conventional methods of analysis. Other parameters and results of interest are also tabulated in Table II.

TABLE II

| Example | R₄P⊕Cl⊖ | Phenol | Salt Mole Ratio R₄P⊕:(HX + X⊖) | Isolated Yield |
|---|---|---|---|---|
| 13 | Benzyltriphenyl P⊕Cl⊖ | Bisphenol A | 1:2 | 95.0 |
| 14 | Benzyltriphenyl P⊕Cl⊖ | 2,2',6,6'-tetrabromo-bisphenol A | 1:1 | 97.0 |
| 15 | Methyltriphenyl P⊕Cl⊖ | 2,2',6,6'-tetrabromo-bisphenol A | 1:1 | 96.5 |
| 16 | Methyl(tri-n-butyl) P⊕Cl⊖ | 2,2',6,6'-tetrabromo-bisphenol A | 1:1 | * |
| 17 | Methyl(tri-n-butyl) P⊕Cl⊖ | Bisphenol A | 1:2 | * |
| 18 | Benzyl(tri-n-butyl) P⊕Cl⊖ | Bisphenol A | 1:2 | * |
| 19 | Benzyl(tri-n-butyl) P⊕Cl⊖ | 2,2',6,6'-tetrabromo-bisphenol A | 1:1 | * |
| 20 | Tetraphenyl P⊕Cl⊖ | 2,2',6,6'-tetrabromo-bisphenol A | 1:1 | * |
| 21 | Tetraphenyl P⊕Cl | Bisphenol A | 1:2 | * |
| 22 | Ethyltriphenyl P⊕Cl⊖ | 2,2',6,6'-tetrabromo-bisphenol A | 1:1 | * |

*Not determined.

EXAMPLES 23-26

A stirred methanol solution containing 45 grams (0.113 mole) of n-butyl triphenyl phosphonium bromide salt is contacted for 10 minutes sequentially with five 31-gram portions of a quaternary ammonium-type, styrene-divinylbenzene anion-exchange resin bearing 3.5 milliequivalents of exchangeable hydroxide groups per gram. After each contact, the methanol solution is separated from the resin and combined with methanol washes of the partially exchanged resin. This procedure produced an 8 percent solution of n-butyl triphenyl phosphonium hydroxide salt.

In a manner otherwise similar to that described in Example 1, the phenols listed in Table III are reacted with the n-butyl triphenyl phosphonium hydroxide salt prepared as described immediately above. The crude product is then isolated from the methanol reaction mixture, dried and weighed. Conventional methods of analysis are utilized to identify the product and in each instance the product is an n-butyl triphenyl phosphonium salt of the phenol reacted as expected. The mole ratio of the phosphonium hydroxide salt to the phenol added to the reaction mixture, the mole ratio of the phosphonium cation to the total phenoxide and phenol in the product salt and the isolated yield of the product in mole percent are tabulated in Table III.

TABLE III

| Example | Phenol | Reaction Mole Ratio R₄P⊕OH:HX | Salt Mole Ratio R₄P⊕:(HX + X⊖) | Isolated Yield |
|---|---|---|---|---|
| 23 | 4,4'-Dihydroxy-diphenyl-ether | 1:2.4 | 1:2 | 76 |
| 24 | Phenolphthalein | 1:2 | 1:2 | 76 |
| 25 | Resorcinol | 1:2 | 1:2 | 90 |
| 26 | 2,2'-Dihydroxy-biphenyl | 1:2 | 1:2 | 76 |

EXAMPLE 27

An aqueous solution of 50 percent sodium hydroxide (5.02 grams, 0.0627 mole) at 20° C. is added to a stirred reaction mixture of 25 grams (0.0626 mole) n-butyltriphenyl phosphonium bromide in 37.5 milliliters (ml) of methanol cooled to a temperature of 5° C. The rate of sodium hydroxide addition is controlled so that the temperature of the reaction mixture does not exceed 15° C. After addition of the sodium hydroxide is complete, the temperature of the stirred reaction mixture is permitted to rise to 18° C. over a period of 15 minutes. A solution of 28.54 grams (0.125 mole) of bisphenol A in 34.0 ml of methanol is rapidly added at 20° C. to the stirred reaction mixture. The reaction mixture is stirred for an additional 10 minutes, followed by the addition of 12.5 grams of deionized water to the mixture, and stirring for 60 more minutes. A white crystalline precipitate is recovered by filtration of the reaction mixture. This crude product is washed with deionized water and dried to a weight of 46.0 grams. Conventional methods of analysis are utilized to identify the product as a 1:2 n-butyl triphenyl phosphonium salt complex of bisphenol A. The yield of the product based on the corresponding phosphonium hydroxide salt is 92.7 mole percent.

EXAMPLE 28

A solution of 28.54 grams (0.125 mole) of bisphenol A in 34.0 ml of methanol at 20° C. is added to a stirred reaction mixture of 25 grams of n-butyl triphenyl phosphonium bromide in 37.5 ml of methanol. An aqueous solution of 50 percent sodium hydroxide (5.02 grams, 0.0627 mole) at 20° C. is then added to the reaction mixture with cooling and at a slow rate so that the temperature of the mixture does not exceed 25° C. The reaction mixture is stirred for an additional 10 minutes, followed by the addition of 12.5 grams of deionized water to the mixture and stirring for 60 more minutes. A white crystalline precipitate is recovered by filtration of the reaction mixture. This crude product is washed with deionized water and dried to a weight of 48.4 grams. Conventional methods of analysis are utilized to identify the product as a 1:2 n-butyltriphenyl phosphonium salt complex of bisphenol A. The yield of the product based on the corresponding phosphonium hydroxide salt is 96 mole percent.

EXAMPLE 29

To a reaction vessel equipped with means for stirring and temperature indication is charged 141.37 grams of the diglycidyl ether of bisphenol A (DGEBA) having an epoxy equivalent weight of 183, 82.08 grams of bisphenol A and 74.5 grams of ethylene glycol ethyl ether. The DGEBA contains 0.375 percent total chlorine and 311 ppm of hydrolyzable chlorine. The reaction mixture is heated to about 50° C. and then 2.59 grams (1.11 percent of reactants) of the 1:1 n-butyl triphenyl phosphonium salt of 2,2',6,6'-tetrabromobisphenol A described in Example 1 is introduced with stirring. The stirred reaction mixture is rapidly heated to 110° C. and then more slowly heated over a period of 30 minutes to 130° C. and maintained at the latter temperature for 165 minutes. A small sample of the reaction mixture is analyzed by conventional methods and it is determined that about 95.5 percent of the epoxy moieties and 98.7 percent of the phenolic hydroxyl groups have reacted.

Next 8.16 grams of 2,2',6,6'-tetrabromobisphenol A and 50.2 grams of ethylene glycol ethyl ether is added to the reaction mixture. It is desirable to utilize as little of the ethylene glycol ethyl ether solvent as is possible to maximize the weight-average molecular weight of the product resin; however, as the reaction mixture becomes too viscous to stir effectively, it is necessary to add additional amounts of the solvent. After 50 minutes at 130° C., it is necessary to add an additional 29.7 grams of ethylene glycol ethyl ether to the reaction mixture and after 65 additional minutes another 77.4 grams of solvent is added. The reaction mixture is stirred for 65 more minutes at 130° C., then 463 grams of ethylene glycol ethyl ether is added to the reaction mixture and the mixture is stirred to effect a homogeneous solution of the resin product. The weight-average molecular weight of the product resin in the solution as determined by gel permeation chromatography (GPC) is 123,825.

The homogeneous resin product solution at 25° C. is removed and diluted with an equal weight of ethylene glycol ethyl ether. This dilute product solution is added with vigorous stirring to 3,500 grams of methanol. The resulting resin product slurry is stirred for ten minutes and then the resin is collected by filtration. The resin is dried to a constant weight of 220 grams. The precipitated resin is determined by gel permeation chromatography to possess a weight-average molecular weight ($M_w$) of 120,192 and a number-average molecular weight of 14,855 ($M_n$).

About 37 grams of this ultra-high molecular weight (UHMW) resin is then molded into a 2.75"×5" by one-eighth inch thick sheet in a heated press at a ram pressure of 15 tons. This sheet is then cut into strips suitable for testing the tensile strength, impact strength, flexural strength and hardness of the molded resin. Test strips of a high-molecular weight epoxy resin ($M_w$=39,800, $M_n$=7,000) sold commercially by Union Carbide Company under the tradename "PKHH" are prepared in a like manner for purposes of comparison. All tests are performed in accordance with standard methods approved by the American Society for Testing and Materials (ASTM) in Part 27. The molding temperature for each sheet and the relevant test data is set out in Table IV.

TABLE IV

| ASTM Test# | Property Tested | Materials Tested | |
|---|---|---|---|
| | | PKHH* | UHMW Resin |
| — | Molding Temperature | 177° C. | 240° C. |
| D-638-68 | Yield Tensile Strength (psi) | 8,684 | 9,980 |
| " | Yield Elongation (%) | 3.33 | 3.84 |
| D-790-66 Method I | Flexural Strength (psi) | 14,679 | 15,866 |
| " | Flexural Modulus of Elasticity (psi) | 419,900 | 396,900 |
| D-2583-67 | Barcol Hardness | 14 | 9 |
| D-256-56 | Izod Impact Strength | | |

TABLE IV-continued

| ASTM Test# | Property Tested | Materials Tested | |
|---|---|---|---|
| | | PKHH* | UHMW Resin |
| Method A | (foot-pounds/inch) | 1.63 | 1.21 |

*Not an embodiment of this invention.
PKHH — tradename of a high molecular weight epoxy resin sold by Union Carbide Company

EXAMPLES 30–35

In the manner described in Example 29, a reaction vessel is charged with DGEBA, bisphenol A and an ethylene glycol ethyl ether solvent. The reaction mixture is heated to 50° C. and then a quantity of an n-butyltriphenyl or triphenylmethyl phosphonium phenoxide catalyst (from 0.65 to 1.70 percent of the reactants) as tabulated in Table IV is introduced. The general procedure for preparing a 25 percent solution of an ultra high molecular weight resin product in an ethylene glycol ethyl ether described in Example 29 is then followed. The weight-average molecular weight of the product resin in the solution as determined by GPC is also determined and tabulated.

TABLE V

| Example | P⊕ Phenoxide Salt | Catalyst (Wt. %) | $M_w$ |
|---|---|---|---|
| 30 | 1:2 $(C_6H_5)_3P^\oplus$ $(C_4H_9)$ Salt of Bisphenol A | 0.71 | 79,640 |
| 31 | 1:2 $(C_6H_5)_3P^\oplus$ $(CH_3)$ Salt of Bisphenol A | 0.65 | 70,740 |
| 32 | 1:1 $(C_6H_5)_3P^\oplus$ $(C_4H_9)$ Salt of Tetrabromobisphenol A | 0.65 | 71,050 |
| 33 | 1:1 $(C_6H_5)_3P^\oplus$ $(C_4H_9)$ Salt of Tetrabromobisphenol A | 1.68 | 142,210 |
| 34 | 1:1 $(C_6H_5)_3P^\oplus$ $(C_4H_9)$ Salt of Tetrabromobisphenol A | 1.70 | 121,930 |
| 35 | 1:1 $(C_6H_5)_3P^\oplus$ $(C_4H_9)$ Salt of Tetrachlorobisphenol A | 1.69 | 118,810 |

The data in Table V suggest that to produce resins having ultra-high molecular weights relatively greater catalyst loadings must be employed than used to produce those of relatively lower molecular weights.

EXAMPLE 36

To a reaction vessel equipped with means for stirring, heating and temperature indication is charged at 20° C. under nitrogen purge with 67.0 parts of bisphenol A, 133.0 parts of DGEBA having an epoxy equivalent weight (EEW) of 187 and 0.484 parts of a 1:1 n-butyltriphenyl phosphonium salt of 2,2',6,6'-tetrabromobisphenol A. This stirred reaction mixture is warmed at a rate of 3° C. per minute to about 150° C. External heating is discontinued at 150° C., but the exotherm of the reaction heats the mixture to a peak temperature of about 222° C. The reaction mixture is permitted to cool to 160° C. and maintained at that temperature for 30 minutes.

The observed epoxy content of the resin product determined by conventional wet analysis technique is 2.36 percent, almost as great as the theoretical epoxy content of a linear advanced epoxy resin 2.39 percent. A substantially linear epoxy resin of excellent color is provided.

EXAMPLE 37

In a manner similar to that described in Example 36 a reaction mixture of 0.396 parts of 1:2 n-butyltriphenyl phosphonium salt of bisphenol A, 64.0 parts of bisphenol A and 136.0 parts of DGEBA is warmed to 150° C. and then allowed to heat in accordance with the reaction exotherm. The reaction mixture is then permitted to cool from its peak temperature of 244° C. to 160° C., where the temperature is maintained for thirty minutes.

The observed epoxy content of the resin product determined by conventional wet analysis technique is 4.64 percent; almost identical to the theoretical epoxy content of 4.65 percent. A substantially linear epoxy resin of excellent color is provided.

EXAMPLE 38

To a reaction vessel equipped with means for stirring and controlling temperature is charged at 20° C. under a nitrogen purge a mixture of 87 parts of bisphenol A and 200 parts of DGEBA having an EEW of 187.7. This stirred reaction mixture is warmed to a temperature of 100° C. over a period of 30 minutes and then 0.428 parts of a 1:2 n-butyltriphenyl phosphonium salt of bisphenol A is introduced. The temperature of the mixture is controlled during the reaction so that it does not exceed 200° C. After the exothermic reaction slows, the mixture is heated at 190° C. for 2 hours.

The observed epoxy content of the resin product determined by conventional wet analysis technique is 4.34 percent; almost as great as the theoretical epoxy content of 4.65 percent. A substantially linear epoxy resin of excellent color is provided. This resin differs from the resin prepared in Example 37 in that molded articles produced from the former have somewhat better heat distortion properties than those produced from the latter resin.

EXAMPLE 39

To a reaction vessel equipped with means for stirring and temperature indication is charged at 20° C. under nitrogen purge 10.3 grams (0.05 mole) of 4-t-butylphenyl glycidyl ether, 3.6 grams (0.05 mole) of acrylic acid and 0.014 gram of the 1:2 n-butyltriphenyl phosphonium salt of bisphenol A. The reaction mixture is stirred at a temperature of 115° C. for a period of five hours. The reaction mixture is titrated with base at the end of the reaction period and less than 1 percent of the acrylic acid added is determined to be unreacted. Infrared spectroscopy and other conventional methods of analysis are utilized to identify the product as corresponding to the formula

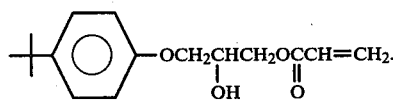

In contrast, only a 28 percent yield of product is obtained in a similar experiment conducted without the catalyst. This example demonstrates the efficacy of the tetrahydrocarbyl phosphonium phenoxide salt in promoting the reaction of a carboxylic acid with an epoxide.

EXAMPLE 40

To a reaction vessel equipped with means for stirring and temperature indication is charged at 20° C. under nitrogen purge 9.4 grams (0.1 mole) of phenol, 4.84 grams (0.11 mole) of ethylene oxide and 0.014 gram of the 1:2 n-butyltriphenyl phosphonium salt of bisphenol A. The reaction mixture is stirred at a temperature of 150° C. for a period of 3 hours. The reaction mixture is first cooled and then analyzed by conventional methods of analysis. The product is identified as 93.8 percent ethylene glycol phenyl ether and 6.0 percent diethylene glycol phenyl ether. The conversion of the phenol to the above-identified product is 99.7 percent.

EXAMPLE 41

To a reaction vessel equipped with means for stirring and temperature indication is charged at 20° C. 423.9 grams of the diglycidyl ether of bisphenol A (DGEBA) having an epoxy equivalent weight of 188.73 and 136.7 grams of bisphenol A. The reaction mixture is heated to 70° C. and then 0.57 grams of 1:1 n-butyltriphenyl phosphonium salt of 2,2',6,6'-tetrabromobisphenol A is introduced with stirring. The mixture is rapidly heated to 90° C. and then more slowly over a period of 30 minutes is heated to 150° C. The reaction mixture is maintained at 150° C. for 1.5 hours and then allowed to cool. Another 143.21 grams of DGEBA is added to the reaction mixture at a temperature of 120° C. After 10 minutes, a small sample of the reaction mixture is analyzed by conventional methods to determine an epoxide content of 11.08 percent and an epoxy equivalent weight of 388.01. Thus, the epoxy resin has been partially advanced.

The partially advanced epoxy resin product is purged with air and then combined with 0.19 gram hydroquinone (a vinyl polymerization inhibitor), 155.59 grams methacrylic acid and 1.1 grams tridimethyl aminomethyl phenol (a curing accelerator) at 115° C. After 5.5 hours, a sample of the vinyl ester resin is taken and 850 grams of styrene is introduced to the remaining vinyl ester resin to reduce the viscosity of the product mixture. Analysis of the sample of vinyl ester resin product by conventional methods indicates an acid content of 0.97 percent and an epoxide content of 0.83 percent.

The styrene/vinyl ester resin mixture is cured at a temperature of about 75° C. in the presence of cobalt naphthenate and methyl ethyl ketone peroxide in the conventional manner. The cured vinyl ester resin-styrene copolymer possesses the physical properties tabulated in Table VI.

TABLE VI

| ASTM Test # | Property Tested | Test Result |
| --- | --- | --- |
| D-638-68 | Yield Tensile Strength | 12,278 psi |
| D-638-68 | Yield Elongation | 5.52% |
| D-790-66 Method | Flexural Strength | 12,193 psi |
| D-790-66 Method | Flexural Modulus of Elasticity | 554,000 psi |
| D-2583-67 | Barcol Hardness | 26.2 |

It is apparent from the data tabulated in Table VI that the vinyl ester resins produced from epoxy resins advanced with the catalysts of this invention possess useful properties.

EXAMPLE 42

A methanol solution of sodium hydroxide (4.0 grams, 0.1 mole) at 20° C. is added slowly to a stirred reaction mixture of ethyltriphenyl phosphonium bromide (37.13 grams, 0.1 mole) in 37.0 grams of methanol cooled to a reaction temperature of 10° C. The rate of sodium hydroxide addition is controlled, so that the temperature of the reaction mixture does not exceed 10° C. After addition of the sodium hydroxide is complete, the reaction mixture is stirred for one hour and then filtered through a sintered glass funnel. The recovered solid, sodium bromide, is washed with cold, anhydrous methanol and dried to yield 10.0 grams (97.17 percent yield).

A methanol solution of bisphenol A (11.4 grams, 0.05 mole) at 20° C. is added slowly to the stirred filtrate containing ethyltriphenyl phosphonium hydroxide at 10° C. After stirring at 10° C. for one hour, the excess methanol solvent is removed by vacuum distillation technique (50° C., 0.1 mm) to yield a light-yellow solid; the reaction mixture yielded 40.1 grams (97.0 percent) of the product. Conventional methods of analysis are used to identify the product as an ethyltriphenyl phosphonium salt of bisphenol A complexed with an ethyltriphenyl phosphonium hydroxide.

This solid product is treated by stirring it in acetone at 25° C. for ten minutes. The acetone is filtered to recover 28.0 grams of a white solid product, which is identified as the uncomplexed ethyltriphenyl phosphonium salt of bisphenol A.

EXAMPLE 43

A methanol solution of sodium hydroxide (4.0 grams, 0.1 mole) at 20° C. is added slowly to a stirred reaction mixture of ethyltriphenyl phosphonium bromide (37.13 grams, 0.1 mole) in 37.0 grams of methanol cooled to a reaction temperature of 10° C. The rate of sodium hydroxide addition is controlled, so that the temperature of the reaction mixture does not exceed 10° C. After addition of the sodium hydroxide is complete, the reaction mixture was stirred for one hour and then filtered through a medium sintered glass funnel. The recovered solid, sodium bromide, was washed with cold, anhydrous methanol and dried to yield 10.0 grams (97.17 percent yield).

A methanol solution of bisphenol S (12.5 grams, 0.05 mole) at 20° C. is added slowly to the stirred filtrate containing ethyltriphenyl phosphonium hydroxide at 10° C. After stirring at 10° C. for one hour, the excess methanol solvent is removed by vacuum distillation (50° C., 0.1 mm) to yield a light-yellow solid, the reaction mixture yielded 41.21 grams (97.0 percent) of product. Conventional methods of analysis are used to identify the product as an ethyltriphenyl phosphonium salt of bisphenol S complexed with an ethyltriphenyl phosphonium hydroxide.

EXAMPLE 44

One gram of the 1:2 n-butyl triphenyl phosphonium salt of bisphenol A prepared in Example 2 is charged with stirring to a reaction vessel containing 1000 grams of DGEBA. The stirred precatalyzed resin is maintained at a temperature of 50° C. for six weeks, during which time the viscosity in centipose and the percent epoxide are measured at two-week intervals. The measured parameters are tabulated in Table VII.

At the end of the six-week period, a sufficient quantity of bisphenol A is added to the precatalyzed resin, so that at reactive conditions the resin would be predicted by theory to produce one having an epoxy content of 2.10 percent. The resulting mixture is heated at 160° C. for two hours. The observed epoxy content of the resin product determined by conventional wet analysis is 2.12 percent, virtually the same as the theoretical epoxy content of 2.10 percent.

TABLE VII

| Time (weeks) | Viscosity (centipoise) | Percent Epoxide |
|---|---|---|
| 0 | 10,372 | 23.82 |
| 2 | 10,566 | 23.78 |
| 4 | 10,600 | 23.80 |
| 6 | 10,622 | 23.75 |

What is claimed is:

1. A compound represented by the formula

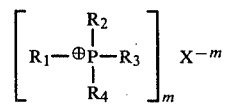

or a complex of the compound represented by Formula I with one or more equivalents of a phenol, $H_mX$, wherein (1) $R_1$–$R_4$ each independently is a hydrocarbyl or inertly-substituted hydrocarbyl;

(2) X is a phenoxide anion, said anion being a conjugate base of a polyhydric phenol bearing from 2 to 6 nuclear hydroxyl groups and having from about 12 to about 30 carbon atoms; and (3) m is the valence of the anion X.

2. The compound defined by claim 1 wherein $R_1$–$R_4$ each independently is phenyl or $C_1$ to $C_{12}$ alkyl or inertly-substituted alkyl.

3. The compound defined by claim 1 wherein $R_1$–$R_4$ each independently is phenyl or $C_1$ to $C_4$ alkyl.

4. The compound defined by claim 1 wherein $R_1$–$R_4$ each independently is phenyl or n-butyl.

5. The compound defined by claim 1 wherein $R_1$ is an n-butyl or ethyl group and $R_2$–$R_4$ are each phenyl.

6. The compound defined by claim 1, 2 or 5 wherein X is derived from a polyhydric phenol corresponding to phenolphthalein or to the formula

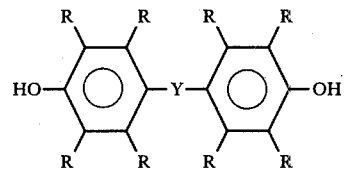

wherein, (1) each R independently is a hydrogen, halogen, hydrocarbyl, inertly-substituted hydrocarbyl or hydrocarbyloxy group;

(2) Y is a single covalent bond, oxygen, sulfur, —CO—, —SO—, —$SO_2$— or lower alkylene or alkylidene of from 1 to 6 carbon atoms, inclusive; and (3) m is the integer 1 or 2.

7. The compound defined by claim 6 wherein each R independently is hydrogen, chlorine or bromine.

8. The compound defined by claim 7 wherein Y is $C_1$–$C_4$ alkylene or alkylidene.

9. The compound defined by claim 8 wherein Y is methylene or isopropylidene.

10. The compound defined by claim 6 wherein X is a phenoxide anion or dianion derived from bisphenol A, bisphenol F, phenolphthalein, 2,2′,6,6′-tetrachlorobisphenol A, bisphenol S, bis(4-hydroxyphenyl), 2-hydroxyphenylmethane or 2,2′,6,6′-tetrabromobisphenol A.

11. The compound defined by claim 10 wherein X is a phenoxide anion or dianion derived from bisphenol A or 2,2′,6,6′-tetrabromobisphenol A.

* * * * *